United States Patent
Ball et al.

(10) Patent No.: US 8,507,279 B2
(45) Date of Patent: Aug. 13, 2013

(54) SYSTEM AND METHOD OF VERIFICATION OF A PREPARED SAMPLE FOR A FLOW CYTOMETER

(75) Inventors: Jack T. Ball, Ann Arbor, MI (US); Grant C. Howes, Ann Arbor, MI (US); Collin A. Rich, Ypsilanti, MI (US)

(73) Assignee: Accuri Cytometers, Inc., Ann Arbor, MI (US)

( * ) Notice: Subject to any disclaimer, the term of this patent is extended or adjusted under 35 U.S.C. 154(b) by 407 days.

(21) Appl. No.: 12/792,536

(22) Filed: Jun. 2, 2010

(65) Prior Publication Data

US 2011/0008816 A1    Jan. 13, 2011

Related U.S. Application Data

(60) Provisional application No. 61/183,328, filed on Jun. 2, 2009.

(51) Int. Cl.
*G01N 31/00*    (2006.01)
*G01N 33/00*    (2006.01)
*G01N 21/01*    (2006.01)
*G01N 21/00*    (2006.01)

(52) U.S. Cl.
USPC ........ 436/10; 436/8; 422/62; 422/67; 422/73; 422/82.05

(58) Field of Classification Search
None
See application file for complete search history.

(56) References Cited

U.S. PATENT DOCUMENTS

| | | | |
|---|---|---|---|
| 3,347,273 A | 10/1967 | Russell | |
| 3,601,128 A | 8/1971 | Hakim | |
| 3,672,402 A | 6/1972 | Bloemer | |
| 3,819,272 A | 6/1974 | Crozier et al. | |
| 4,112,735 A | 9/1978 | McKnight | |
| 4,138,879 A | 2/1979 | Liebermann | |
| 4,371,786 A | 2/1983 | Kramer | |
| 4,448,538 A | 5/1984 | Mantel | |
| 4,559,454 A | 12/1985 | Kramer | |
| 4,570,639 A | 2/1986 | Miodownik | |
| 4,691,829 A | 9/1987 | Auer | |
| 4,755,021 A | 7/1988 | Dyott | |
| 4,790,653 A | 12/1988 | North, Jr. | |
| 4,818,103 A | 4/1989 | Thomas et al. | |
| 4,824,641 A | 4/1989 | Williams | |
| 4,826,660 A | 5/1989 | Smith et al. | |
| 4,844,610 A | 7/1989 | North, Jr. | |

(Continued)

FOREIGN PATENT DOCUMENTS

| | | |
|---|---|---|
| EP | 466490 A | 1/1992 |
| EP | 1391611 A | 2/2004 |

(Continued)

OTHER PUBLICATIONS

U.S. Appl. No. 12/476,877, filed Jun. 2, 2009, Ball et al.

*Primary Examiner* — Neil N Turk
(74) *Attorney, Agent, or Firm* — Jeffrey Schox

(57) ABSTRACT

A system and method for a flow cytometer system including a prepared sample fluid with reference beads; an interrogation zone that analyzes the prepared sample fluid; a peristaltic pump system that draws the sample fluid through the interrogation zone; and a processor that monitors a measured volume of sample fluid sampled by the peristaltic pump system and an expected sample volume based on data generated by the analysis of the sample fluid. A system and method is additionally described using an alternative volume sensing fluidic system.

16 Claims, 8 Drawing Sheets

(56) References Cited

U.S. PATENT DOCUMENTS

| | | |
|---|---|---|
| 4,933,813 A | 6/1990 | Berger |
| 5,028,127 A | 7/1991 | Spitzberg |
| 5,040,890 A | 8/1991 | North, Jr. |
| 5,043,706 A | 8/1991 | Oliver |
| 5,083,862 A | 1/1992 | Rusnak |
| 5,138,868 A | 8/1992 | Long |
| 5,139,609 A | 8/1992 | Fields et al. |
| 5,150,037 A | 9/1992 | Kouzuki |
| 5,150,313 A | 9/1992 | van den Engh et al. |
| 5,155,543 A | 10/1992 | Hirako |
| 5,204,884 A | 4/1993 | Leary et al. |
| 5,224,058 A | 6/1993 | Mickaels et al. |
| 5,230,026 A | 7/1993 | Ohta |
| 5,270,548 A | 12/1993 | Steinkamp |
| 5,301,685 A | 4/1994 | Guirguis |
| 5,308,990 A | 5/1994 | Takahashi et al. |
| 5,367,474 A | 11/1994 | Auer et al. |
| 5,374,395 A | 12/1994 | Robinson et al. |
| 5,395,588 A | 3/1995 | North, Jr. et al. |
| 5,403,552 A | 4/1995 | Pardikes |
| 5,466,946 A | 11/1995 | Kleinschmitt et al. |
| 5,469,375 A | 11/1995 | Kosaka |
| 5,539,386 A | 7/1996 | Elliott |
| 5,552,885 A | 9/1996 | Steen |
| 5,559,339 A | 9/1996 | Domanik et al. |
| 5,616,124 A | 4/1997 | Hague et al. |
| 5,684,480 A | 11/1997 | Jansson |
| 5,739,902 A | 4/1998 | Gjelsnes et al. |
| 5,797,430 A | 8/1998 | Becke et al. |
| 5,798,222 A | 8/1998 | Goix |
| 5,804,507 A | 9/1998 | Perlov et al. |
| 5,883,378 A | 3/1999 | Irish et al. |
| 5,920,388 A | 7/1999 | Sandberg et al. |
| 5,960,129 A | 9/1999 | Kleinschmitt |
| 5,981,180 A | 11/1999 | Chandler et al. |
| 6,016,376 A | 1/2000 | Ghaemi et al. |
| 6,039,078 A | 3/2000 | Tamari |
| 6,067,157 A | 5/2000 | Altendorf |
| 6,070,477 A | 6/2000 | Mark |
| 6,091,502 A | 7/2000 | Weigl et al. |
| 6,097,485 A | 8/2000 | Lievan |
| 6,108,463 A | 8/2000 | Herron et al. |
| 6,110,427 A | 8/2000 | Uffenheimer |
| 6,115,065 A | 9/2000 | Yadid-Pecht et al. |
| 6,139,800 A | 10/2000 | Chandler |
| 6,154,276 A | 11/2000 | Mariella, Jr. |
| 6,156,208 A | 12/2000 | Desjardins et al. |
| 6,181,319 B1 | 1/2001 | Fujita et al. |
| 6,183,697 B1 | 2/2001 | Tanaka et al. |
| 6,288,783 B1 | 9/2001 | Auad |
| 6,377,721 B1 | 4/2002 | Walt et al. |
| 6,382,228 B1 | 5/2002 | Cabuz et al. |
| 6,403,378 B1 | 6/2002 | Phi-Wilson et al. |
| 6,427,521 B2 | 8/2002 | Jakkula et al. |
| 6,431,950 B1 | 8/2002 | Mayes |
| 6,456,769 B1 | 9/2002 | Furusawa et al. |
| 6,469,787 B1 | 10/2002 | Meyer et al. |
| 6,473,171 B1 | 10/2002 | Buttry et al. |
| 6,519,355 B2 | 2/2003 | Nelson |
| 6,522,775 B2 | 2/2003 | Nelson |
| 6,568,271 B2 | 5/2003 | Shah et al. |
| 6,587,203 B2 | 7/2003 | Colon |
| 6,602,469 B1 | 8/2003 | Maus et al. |
| 6,636,623 B2 | 10/2003 | Nelson et al. |
| 6,675,835 B2 | 1/2004 | Gerner et al. |
| 6,694,799 B2 | 2/2004 | Small |
| 6,700,130 B2 | 3/2004 | Fritz |
| 6,710,871 B1 | 3/2004 | Goix |
| 6,718,415 B1 | 4/2004 | Chu |
| 6,778,910 B1 | 8/2004 | Vidal et al. |
| 6,809,804 B1 | 10/2004 | Yount et al. |
| 6,816,257 B2 | 11/2004 | Goix |
| 6,825,926 B2 | 11/2004 | Turner et al. |
| 6,852,284 B1 | 2/2005 | Holl et al. |
| 6,859,570 B2 | 2/2005 | Walt et al. |
| 6,869,569 B2 | 3/2005 | Kramer |
| 6,872,180 B2 | 3/2005 | Reinhardt et al. |
| 6,890,487 B1 | 5/2005 | Sklar et al. |
| 6,897,954 B2 | 5/2005 | Bishop et al. |
| 6,901,964 B2 | 6/2005 | Kippe et al. |
| 6,908,226 B2 | 6/2005 | Siddiqui et al. |
| 6,912,904 B2 | 7/2005 | Storm, Jr. et al. |
| 6,936,828 B2 | 8/2005 | Saccomanno |
| 6,941,005 B2 | 9/2005 | Lary et al. |
| 6,944,322 B2 | 9/2005 | Johnson et al. |
| 7,009,189 B2 | 3/2006 | Saccomanno |
| 7,012,689 B2 | 3/2006 | Sharpe |
| 7,019,834 B2 | 3/2006 | Sebok et al. |
| 7,024,316 B1 | 4/2006 | Ellison et al. |
| 7,061,595 B2 | 6/2006 | Cabuz et al. |
| 7,075,647 B2 | 7/2006 | Christodoulou |
| 7,105,355 B2 | 9/2006 | Kurabayashi et al. |
| 7,106,442 B2 | 9/2006 | Silcott et al. |
| 7,113,266 B1 | 9/2006 | Wells |
| 7,130,046 B2 | 10/2006 | Fritz et al. |
| 7,232,687 B2 | 6/2007 | Lary et al. |
| 7,262,838 B2 | 8/2007 | Fritz |
| 7,274,316 B2 | 9/2007 | Moore |
| 7,328,722 B2 | 2/2008 | Rich et al. |
| 7,362,432 B2 | 4/2008 | Roth |
| 7,403,125 B2 | 7/2008 | Rich |
| 7,471,393 B2 | 12/2008 | Trainer |
| 7,520,300 B2 | 4/2009 | Rich et al. |
| 7,628,956 B2 | 12/2009 | Jindo |
| 7,738,099 B2 | 6/2010 | Morrell et al. |
| 7,739,060 B2 | 6/2010 | Goebel et al. |
| 7,776,268 B2 | 8/2010 | Rich |
| 7,780,916 B2 | 8/2010 | Bair et al. |
| 7,843,561 B2 | 11/2010 | Rich |
| 7,857,005 B2 | 12/2010 | Rich et al. |
| 7,903,706 B2 | 3/2011 | O'Shaughnessy et al. |
| 7,981,661 B2 | 7/2011 | Rich |
| 7,996,188 B2 | 8/2011 | Olson et al. |
| 8,017,402 B2 | 9/2011 | Rich |
| 8,031,340 B2 | 10/2011 | Rich et al. |
| 2001/0014477 A1 | 8/2001 | Pelc et al. |
| 2001/0039053 A1 | 11/2001 | Liseo et al. |
| 2002/0028434 A1 | 3/2002 | Goix et al. |
| 2002/0049782 A1 | 4/2002 | Herzenberg |
| 2002/0059959 A1 | 5/2002 | Qatu et al. |
| 2002/0080341 A1 | 6/2002 | Kosaka |
| 2002/0123154 A1 | 9/2002 | Burshteyn et al. |
| 2002/0192113 A1 | 12/2002 | Uffenheimer et al. |
| 2003/0035168 A1 | 2/2003 | Qian et al. |
| 2003/0048539 A1 | 3/2003 | Oostman et al. |
| 2003/0054558 A1 | 3/2003 | Kurabayashi et al. |
| 2003/0062314 A1 | 4/2003 | Davidson et al. |
| 2003/0072549 A1 | 4/2003 | Facer et al. |
| 2003/0078703 A1 | 4/2003 | Potts et al. |
| 2003/0129090 A1 | 7/2003 | Farrell |
| 2003/0134330 A1 | 7/2003 | Ravkin et al. |
| 2003/0148379 A1 | 8/2003 | Roitman et al. |
| 2003/0175157 A1 | 9/2003 | Micklash, II et al. |
| 2003/0202175 A1 | 10/2003 | van den Engh et al. |
| 2003/0211009 A1 | 11/2003 | Buchanan |
| 2003/0223061 A1 | 12/2003 | Sebok et al. |
| 2003/0235919 A1 | 12/2003 | Chandler |
| 2004/0031521 A1 | 2/2004 | Vrane et al. |
| 2004/0048362 A1 | 3/2004 | Trulson et al. |
| 2004/0112808 A1 | 6/2004 | Takagi et al. |
| 2004/0119974 A1 | 6/2004 | Bishop et al. |
| 2004/0123645 A1 | 7/2004 | Storm et al. |
| 2004/0131322 A1 | 7/2004 | Ye et al. |
| 2004/0143423 A1 | 7/2004 | Parks et al. |
| 2004/0175837 A1 | 9/2004 | Bonne et al. |
| 2004/0197768 A1* | 10/2004 | Glencross .................... 435/4 |
| 2004/0201845 A1 | 10/2004 | Quist et al. |
| 2004/0246476 A1 | 12/2004 | Bevis et al. |
| 2005/0044110 A1 | 2/2005 | Herzenberg |
| 2005/0047292 A1 | 3/2005 | Park et al. |
| 2005/0057749 A1 | 3/2005 | Dietz et al. |
| 2005/0069454 A1 | 3/2005 | Bell |
| 2005/0073686 A1 | 4/2005 | Roth et al. |
| 2005/0078299 A1 | 4/2005 | Fritz et al. |

| | | |
|---|---|---|
| 2005/0105091 A1 | 5/2005 | Lieberman et al. |
| 2005/0162648 A1 | 7/2005 | Auer et al. |
| 2005/0163663 A1 | 7/2005 | Martino et al. |
| 2005/0195605 A1 | 9/2005 | Saccomanno et al. |
| 2005/0195684 A1 | 9/2005 | Mayer |
| 2005/0252574 A1 | 11/2005 | Khan et al. |
| 2006/0002634 A1 | 1/2006 | Riley et al. |
| 2006/0015291 A1 | 1/2006 | Parks et al. |
| 2006/0023219 A1 | 2/2006 | Meyer et al. |
| 2006/0161057 A1 | 7/2006 | Weber |
| 2006/0177937 A1 | 8/2006 | Kurabayashi et al. |
| 2006/0219873 A1 | 10/2006 | Martin et al. |
| 2006/0280061 A1 | 12/2006 | Koreeda et al. |
| 2006/0281143 A1 | 12/2006 | Liu et al. |
| 2006/0286549 A1 | 12/2006 | Sohn et al. |
| 2007/0003434 A1 | 1/2007 | Padmanabhan et al. |
| 2007/0041013 A1 | 2/2007 | Fritz et al. |
| 2007/0079653 A1 | 4/2007 | Zuleta et al. |
| 2007/0096039 A1 | 5/2007 | Kapoor et al. |
| 2007/0124089 A1 | 5/2007 | Jochum et al. |
| 2007/0127863 A1 | 6/2007 | Bair et al. |
| 2007/0144277 A1 | 6/2007 | Padmanabhan et al. |
| 2007/0212262 A1 | 9/2007 | Rich |
| 2007/0224684 A1 | 9/2007 | Olson et al. |
| 2007/0243106 A1 | 10/2007 | Rich |
| 2008/0055595 A1 | 3/2008 | Olson et al. |
| 2008/0064113 A1 | 3/2008 | Goix et al. |
| 2008/0092961 A1 | 4/2008 | Bair et al. |
| 2008/0152542 A1 | 6/2008 | Ball et al. |
| 2008/0215297 A1 | 9/2008 | Goebel et al. |
| 2008/0228444 A1 | 9/2008 | Olson et al. |
| 2008/0246949 A1 | 10/2008 | Harris et al. |
| 2009/0104075 A1 | 4/2009 | Rich |
| 2009/0174881 A1 | 7/2009 | Rich |
| 2009/0201501 A1 | 8/2009 | Bair et al. |
| 2009/0202130 A1 | 8/2009 | George et al. |
| 2009/0216478 A1 | 8/2009 | Estevez-Labori |
| 2009/0257339 A1 | 10/2009 | Katayama |
| 2009/0260701 A1 | 10/2009 | Rich et al. |
| 2009/0293910 A1 | 12/2009 | Ball et al. |
| 2010/0008204 A1 | 1/2010 | Bae et al. |
| 2010/0012853 A1 | 1/2010 | Parks |
| 2010/0032584 A1 | 2/2010 | Dayong et al. |
| 2010/0118298 A1 | 5/2010 | Bair et al. |
| 2010/0119298 A1 | 5/2010 | Huang |
| 2010/0302536 A1 | 12/2010 | Ball et al. |
| 2010/0319469 A1 | 12/2010 | Rich |
| 2010/0319786 A1 | 12/2010 | Bair et al. |
| 2011/0058163 A1 | 3/2011 | Rich |
| 2011/0061471 A1 | 3/2011 | Rich et al. |
| 2011/0306031 A1 | 12/2011 | Rich |

FOREIGN PATENT DOCUMENTS

| | | |
|---|---|---|
| EP | 1396736 A | 3/2004 |
| EP | 1521076 | 4/2005 |
| JP | 356169978 A | 12/1981 |
| JP | Sho5913689 | 3/1984 |
| JP | Sho6353901 | 4/1988 |
| JP | 04086546 H | 3/1992 |
| JP | 6194299 A | 7/1994 |
| JP | 06221988 H | 12/1994 |
| JP | 7260084 A | 10/1995 |
| JP | 08201267 H | 8/1996 |
| JP | 09288053 H | 11/1997 |
| JP | 10227737 A | 8/1998 |
| JP | 2001050887 A | 2/2001 |
| JP | 2001170062 A | 6/2001 |
| JP | 2003262201 A | 9/2003 |
| JP | 200477484 | 3/2004 |
| WO | 9956052 | 11/1999 |
| WO | 0194914 | 12/2001 |
| WO | WO 2005/068971 | 1/2005 |
| WO | WO 2005/017499 | 2/2005 |
| WO | WO 2005/091893 | 2/2005 |
| WO | 2005073694 A | 8/2005 |
| WO | WO 2006/055722 | 5/2006 |
| WO | WO 2007/103969 | 3/2007 |
| WO | 2007067577 A | 6/2007 |
| WO | 2007100723 A | 9/2007 |
| WO | 2007136749 A | 11/2007 |
| WO | WO 2008/058217 | 11/2007 |
| WO | WO 2010/101623 | 9/2010 |

* cited by examiner

Direct System Variations

SYSTEM AND METHOD OF VERIFICATION OF A PREPARED SAMPLE FOR A FLOW CYTOMETER

CROSS-REFERENCE TO RELATED APPLICATIONS

This application claims the benefit of U.S. Provisional Application No. 61/183,328, filed on 2 Jun. 2009 and titled "SYSTEM AND METHOD OF VERIFICATION OF A PREPARED SAMPLE FOR A FLOW CYTOMETER", which is incorporated in its entirety by this reference.

TECHNICAL FIELD

This invention relates generally to the flow cytometer field, and more specifically to a new and useful system and method for verification of a prepared sample in the flow cytometer field.

BACKGROUND

The results from a flow cytometer analysis of microscopic particles often depend on a sample fluid prepared by a machine and/or an experimenter. Errors in the preparation of the sample fluid may drastically alter the accuracy and conclusion of the flow cytometer analysis. As a real world example, $CD_4$ tests are used in determining the state of the immune system of a patient and the progression of HIV to AIDS. A $CD_4$ count of 200 or lower is used to indicate that a patient with HIV has AIDS. During this determination, reference beads are added to a blood sample, and counted by a flow cytometer to calculate the volume of blood analyzed by the flow cytometer. The calculated volume of blood and the number of $CD_4$ particles analyzed during the flow cytometer test are used to calculate the $CD_4$ count. An improperly prepared blood sample, such as one where the concentration of reference beads is not as expected, can lead to false positives and a misdiagnosis. Thus, there is a need in the flow cytometer field to create a new and useful system and method for verification of a prepared sample. This invention provides such a new and useful system and method.

DESCRIPTION OF THE PREFERRED EMBODIMENTS

The following description of the preferred embodiments of the invention is not intended to limit the invention to these preferred embodiments, but rather to enable any person skilled in the art of flow cytometers to make and use this invention.

1. Flow Cytometer System for the Verification of a Prepared Sample

Figure 1:
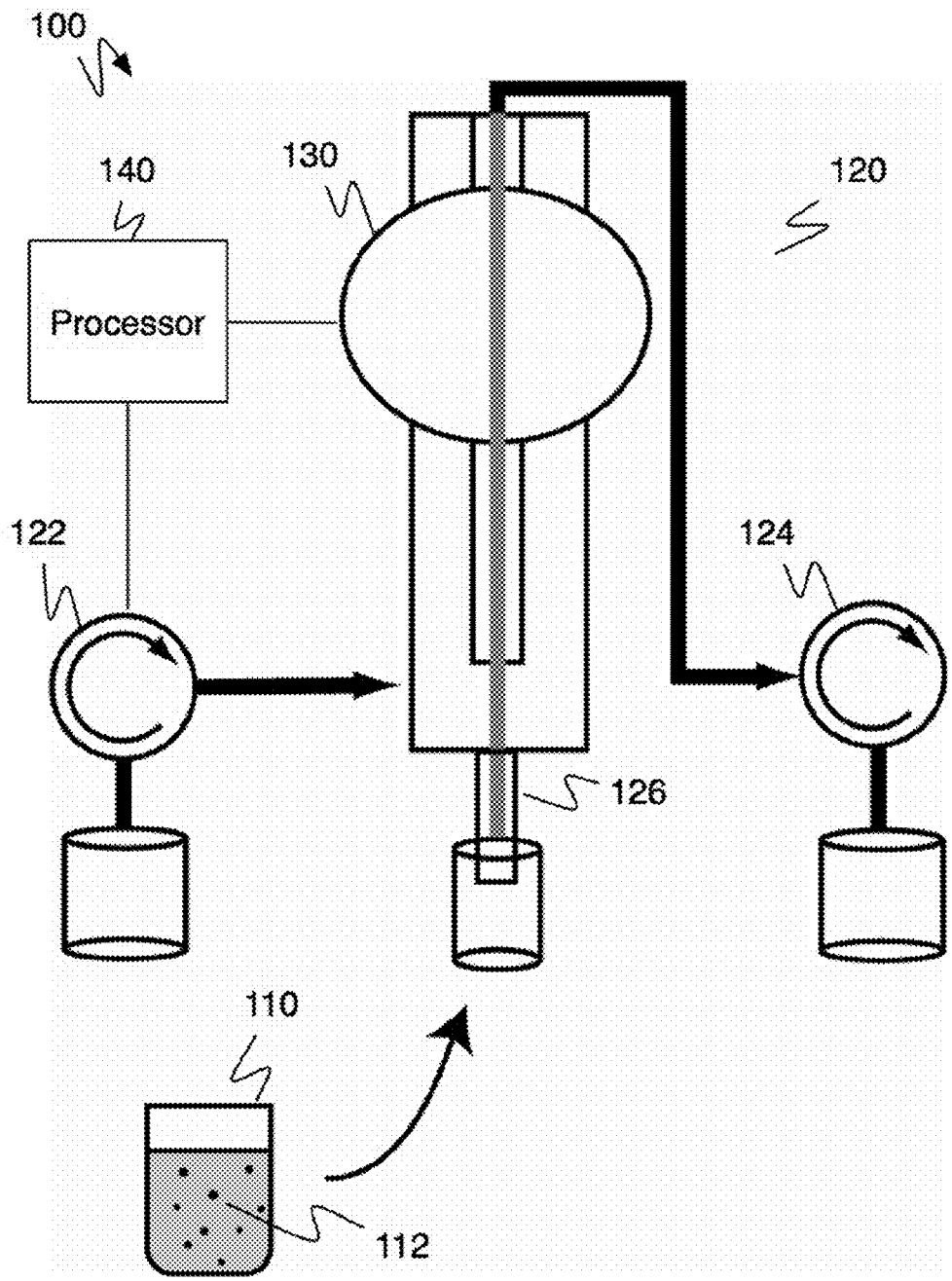
FIG. 1 is a schematic representation of a system of the preferred embodiment of the invention.

As shown in FIG. 1, the flow cytometer system 100 of the preferred embodiment for the verification of a prepared sample includes a sample fluid prepared with beads 110, a peristaltic fluid system 120, an interrogation zone 130, and a processor 140. The peristaltic pump system 120 preferably includes a sheath pump 122, a waste pump 124, and a sample injection probe (SIP) 126. The flow cytometer system 100 functions to compare the actual sample volume as determined by the peristaltic pump system 120 to the expected volume of the prepared sample 110 (as preferably indicated by the reference beads in the sample). Discrepancies in these two volume measurements is preferably handled by flagging data, alerting the experimenter, correcting for volume discrepancies, modification of a sample, and/or any suitable response.

The peristaltic pump system 120 of the preferred embodiment preferably enables the flow cytometer system 100 to monitor the actual volume of sample fluid 110 passing through the interrogation zone 130 with a high level of accuracy due to the unique use of peristaltic pumps. As an exemplary use of the flow cytometer system 100, the prepared sample fluid 110 is preferably prepared with a reagent(s) for a $CD_4$ test. The prepared sample fluid 110 preferably has an expected reference bead concentration. The reference beads of the reagent(s) are preferably counted in the interrogation zone 130, and an expected sample volume based on the reference bead count is preferably calculated. The expected volume based on this data collection is then preferably compared to the volume sampled according to the operation of the peristaltic fluid system 120.

The sample fluid prepared with beads 110 of the preferred embodiment functions to be the fluid with countable microscopic particles for the flow cytometer analysis. The sample fluid 110 preferably includes a sample of blood, but the sample fluid 110 may alternatively be any suitable fluid to be analyzed by the flow cytometer interrogation zone 130. The sample fluid 110 is preferably prepared with an expected concentration and/or volume of diluents (reagents, markers, and/or any suitable fluids). Reference beads 112 are preferably added to the sample fluid 110. The reference beads 112 function to be countable markers or reference particles that are preferably counted by the flow cytometer as the sample fluid passes through the interrogation zone 130. An ideally prepared sample fluid 110 will preferably have a known reference bead count per sample volume. The reference beads 112 may alternatively not be an additive but be a particle with a known concentration in the blood or fluid sample. In one variation, the beads are factory mixed with a test reagent(s) (which includes any necessary reagents) that is used during the preparation of the sample. The reference beads concentration is preferably a well-controlled value for the test reagent(s). The test reagent(s) is then added to the sample fluid during the preparation of the sample. In another variation, the reference beads 112 may alternatively be added or packaged for a set volume of a container (e.g., a test tube). When added to a known volume of fluid the concentration of reference beads will be known. Alternatively, the reference beads 112 may be added separately to the diluent, sample, and/or be added in any suitable means.

Figure 8:
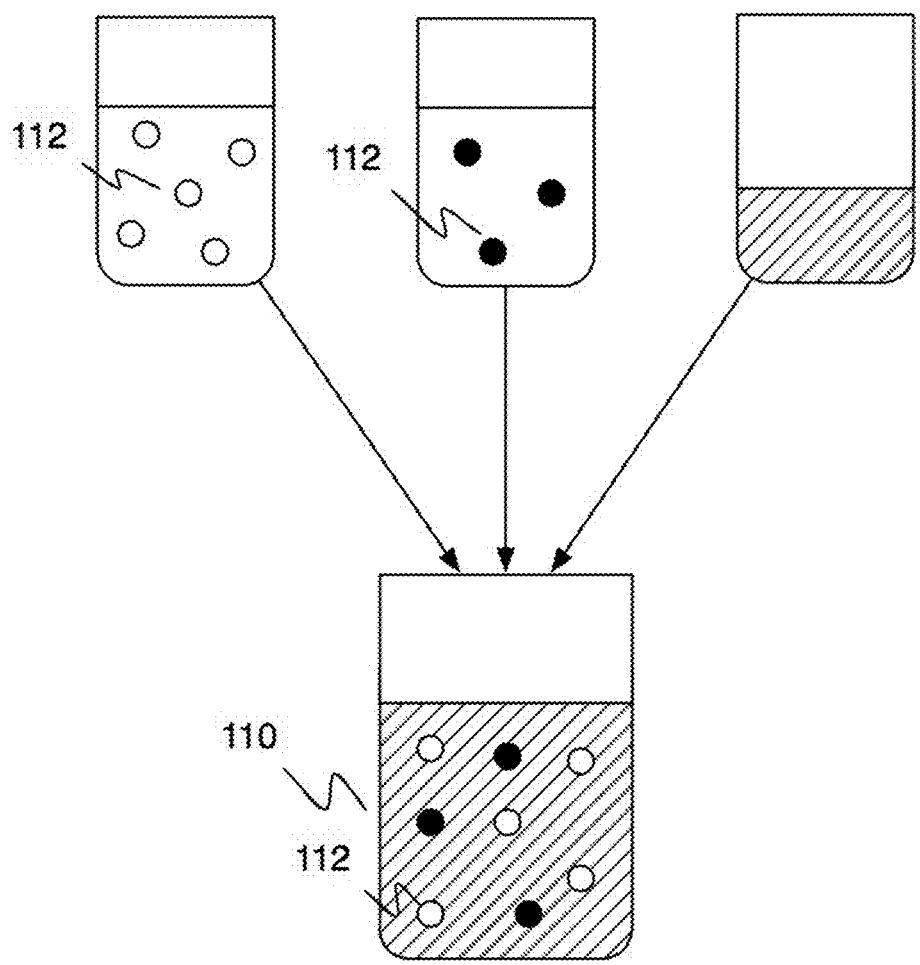
FIG. 8 is a schematic representation of preparing a sample fluid with a plurality of reference bead types.

As an additional variation, the sample fluid may be prepared with a plurality of differing types of reference beads 112. The plurality of types of reference beads 112 preferably functions to create an ratio of reference beads that can be measured by the flow cytometer and compared to an expected reference bead ratio. Additionally, any suitable number of types of regents may alternatively be used. A first type of reference beads 112 can preferably be distinguished from an at least second type of reference beads 112. The plurality of types of reference beads preferably has differing size or fluorescence so that the flow cytometer can distinguish between the two reference beads though any suitable difference may alternatively be used. The flow cytometer can preferably count the number of first reference beads 112 and at least second type of reference beads 112. The first type of reference bead 112 is preferably prepared at a known concentration in a first portion of the sample fluid (e.g., a first reagent), and the at least second type of reference bead is preferably prepared at a known concentration in a second portion of the sample fluid (e.g., a second reagent). The two portions of the sample fluid are preferably combined to form the sample fluid. The ratio of the first type of reference beads to the at least second type of reference beads preferably has an expected value. The flow cytometer can preferably determine the ratio of reference beads in the sample fluid by counting the reference beads. If the expected ratio of reference beads does not substantially match the measured ratio then the sample may have been prepared wrong and any suitable action may be taken. As an example shown in FIG. 8, a liquid antibody reagent containing a known concentration of reference beads A may be added to a blood sample. A lysis reagent containing a concentration of reference beads B is then preferably added to the sample fluid. The quantities of the regents added to the sample fluid can then preferably be verified by measuring the ratio of reference beads A to reference beads B. The ratio preferably has an expected value. If the measured ratio of plurality of reagents is the expected value, and if the correct volume of both the antibody and lysis reagents have been added and the concentration of reference beads is correct then the right amount of blood has been added to the sample fluid.

The peristaltic pump system 120 of the preferred embodiment functions to control the flow of the sample fluid. The peristaltic pump system 120 is preferably the same system shown and disclosed in U.S. patent application Ser. No. 11/370,714 (filed on 8 Mar. 2006 and published on 13 Sep. 2007 as U.S. Pub. No. 2007/0212262), which is hereby incorporated in its entirety. The peristaltic pump system 120 may, however, be any suitable system that functions to control the flow of the sample fluid. The peristaltic pump system preferably has accurate knowledge of the volume of sample fluid that has been passed through the inspection zone. The volume of sample fluid 110 that has passed through the inspection zone is preferably related to the operation of the peristaltic pump system 120. Thus preferably through control and operation of the peristaltic pump system 120, the volume of sample fluid 110 passed through the interrogation zone should be known value. The peristaltic pump system 120 preferably includes a sheath pump 122, a waste pump 124, and a sample injection probe (SIP) 126.

The sheath pump 122 of the preferred embodiment functions to pump sheath fluid from a sheath container into the interrogation zone 130. The sheath fluid functions to hydrodynamically focus the sample fluid. The process of hydrodynamic focusing results in laminar flow of the sample fluid within a flow cell of the interrogation zone of the flow cytometer and enables an optical system to illuminate, and thus analyze, the particles within the sample fluid with uniformity and repeatability. Preferably, the sheath fluid is buffered saline or de-ionized water, but the sheath fluid may alternatively be any suitable fluid to hydrodynamically focus the sample fluid. A sheath container functions to contain the sheath fluid before being pumped. The sheath container is preferably a vented tank with a volume of approximately 1 L, but the sheath tank may alternatively be any suitable container to contain the sheath fluid. Preferably, the sheath pump 122 is a positive displacement pump. More preferably, the sheath pump 122 is a peristaltic pump with a flexible tube and one or more cams that pump the sheath fluid through the flexible tube. The sheath pump 122 preferably has a known flow rate to pump speed ratio, such that control of the speed of the sheath pump 122 corresponds to a control of the flow rate of the sheath fluid. The volume of sheath fluid pumped into the system is preferably derived from the known flow rate to speed value and the speed of the motor. The volume of sheath fluid pumped into the system may alternatively be derived by including a volume sensor (e.g., optical sensor, resistive sensor, etc.) in the sheath container and measuring the decline in volume. A flow rate sensor, volume sensor, or any suitable sensor may alternatively be used. The sheath pump 122 preferably cooperates with the waste pump 124 to draw the sample fluid 110 up through the Sip 130

The waste pump 124 of the preferred embodiment functions to pump the waste fluid from the interrogation zone into a waste container. Preferably, the waste fluid includes the sheath fluid and the sample fluid. Alternatively, the waste fluid may include any fluid that exits the interrogation zone. The waste container is preferably a vented tank with a volume of approximately 1 L, but the waste tank may alternatively be any suitable container to contain the waste fluid. Like the sheath pump 122, the waste pump 124 is preferably a positive displacement pump and more preferably a peristaltic pump with a flexible tube and one or more cams that pump the waste fluid through the flexible tube. The waste pump 124 preferably has a known flow rate to pump speed ratio, such that control of the speed of the waste pump corresponds to a control of the flow rate of the waste fluid. The volume of sheath fluid pumped into the system is preferably derived from the known flow rate to speed value and the speed of the motor. The volume of waste fluid pumped from the system may alternatively be derived by including a volume sensor (e.g., optical sensor, resistive sensor, etc.) in the waste container and measuring the increase in waste volume. A flow rate sensor, volume sensor, or any suitable sensor may alternatively be used.

The sample injection probe (SIP) 126 of the preferred embodiment functions to convey the sample fluid from a sample container into the interrogation zone 130. The sheath pump 122 and the waste pump 124 preferably cooperate to create the fluidic pressure that draws the sample fluid 110 through the SIP 126 into the fluidic system. The SIP 126 is preferably a syringe, drawtube, or any suitable device that functions to convey the sample fluid 110 from the sample container into the interrogation zone 130. The sample container, which functions to contain the sample fluid 110, is preferably an open beaker with a volume of approximately 5 mL, a wellplate, or may alternatively be any suitable container to contain the sample fluid 110.

The interrogation zone 130 of the preferred embodiment functions to inspect the particles of the sample fluid 110. A light source, preferably a laser light source, is preferably directed at the hydrodynamically focused sample fluid 110. Multiple detectors arranged around the interrogation zone preferably detect the scattered or fluorescent light from the particles. Any suitable optical setup or detection method may alternatively be used to count and analyze the particles of the sample fluid 110. The interrogation zone preferably monitors multiple types of particles during any single experiment. Reference beads 112 contained in the prepared sample fluid 110 are preferably counted while analyzing other particles of the sample fluid 110. The expected volume of sample fluid 110 that has been through the interrogation zone 130 can preferably be calculated by relating the reference bead count and the expected concentration of reference beads (where the reference beads are uniformly distributed in the sample fluid).

The processor 140 of the preferred embodiment functions to monitor the status and results of the flow cytometer system. The processor 140 is preferably any suitable processor or computer system, such as a personal computer or an embedded system. The processor 140 is preferably capable of monitoring (e.g., reading or accessing) results from the sample fluid analysis performed in the interrogation zone 130. In particular, the processor 140 preferably monitors the reference bead count data. The reference bead count data may be the total bead count, a time based function of reference bead count, or any suitable data concerning the reference bead count. From the reference bead count data, an expected sample fluid volume is preferably calculated. The expected reference bead concentration is preferably collected by the processor prior to calculating the expected sample fluid volume. An experimenter or alternatively a sample preparation machine preferably enters the reference bead concentration information into the processor via a human computer interface (such as a keyboard and mouse). The information may alternatively be associated with the reagent(s), the type of test, or any suitable parameter. The expected reference bead concentration may alternatively be calculated by the processor 140 from data on the volume of factory prepared reagents (with reference beads) used, and/or from any suitable sample preparation data or information. The processor 140 is additionally capable of accessing, collecting, and/or forming data from the peristaltic pump system 120. In particular, the processor monitors the volume of sheath fluid pumped by the sheath pump 122 and the amount of waste fluid pumped by the waste pump 124. The volume of fluid pumped by a peristaltic pump (based on data such as motor speed/rotation and known flow rate to speed value of the pump) is preferably a well-defined value. The difference between the sheath fluid volume and the waste fluid volume is preferably the actual sample fluid volume (the sample fluid was introduced into the fluidic system via the SIP 126). Alternatively, the actual sample fluid volume may be determined by any suitable means, such as by volume sensors within the sheath fluid tank and waste fluid tank, and/or flow sensors. The processor preferably compares the expected sample fluid volume and the actual sample fluid volume of a sample solution. If the volumes are not the same, the processor 140 preferably flags the data (e.g., displaying a warning to the experimenter), recommends or performs an experimental change (e.g., adjusting the preparation of the sample fluid or subsequent sample fluids), accounts for the discrepancy in volumes (e.g., adjusting data results based on actual reagent concentration), and/or performs any suitable course of action based on the volume difference.

In one example, the flow cytometer system 100 may be used for a $CD_4$ test. A $CD_4$ test is preferably used in the assessment of the immune system and the progress of an HIV infection into AIDS. The $CD_4$ test may involve taking 50 μL of blood and adding 450 μL of reagent(s). In one version, the reagent(s) is preferably a factory prepared solution that contains a known concentration of reference beads. The factory mixed reagent(s) functions to set the reagent(s) to reference bead concentration ratio. In another version, a sample container for a set volume may be provided with the reference beads packaged or pre-added. In yet another version, the reference beads may be added in a controlled manner, by the experimenter and/or by any suitable means. The sample fluid is preferably run through the flow cytometer for analysis. The $CD_4$ (and CD8) cells are preferably counted along with the number of reference beads by the flow cytometer. In the case where the expected sample fluid volume matches the actual sample fluid volume, the concentration of the $CD_4$ (and CD8) cells in the blood is calculated. In the case where the expected sample fluid volume does not match the actual sample fluid volume, the experimenter is preferably alerted to this error and/or any suitable action is taken based on the error.

2. Method of Verifying the Preparation of a Sample

Figure 2:
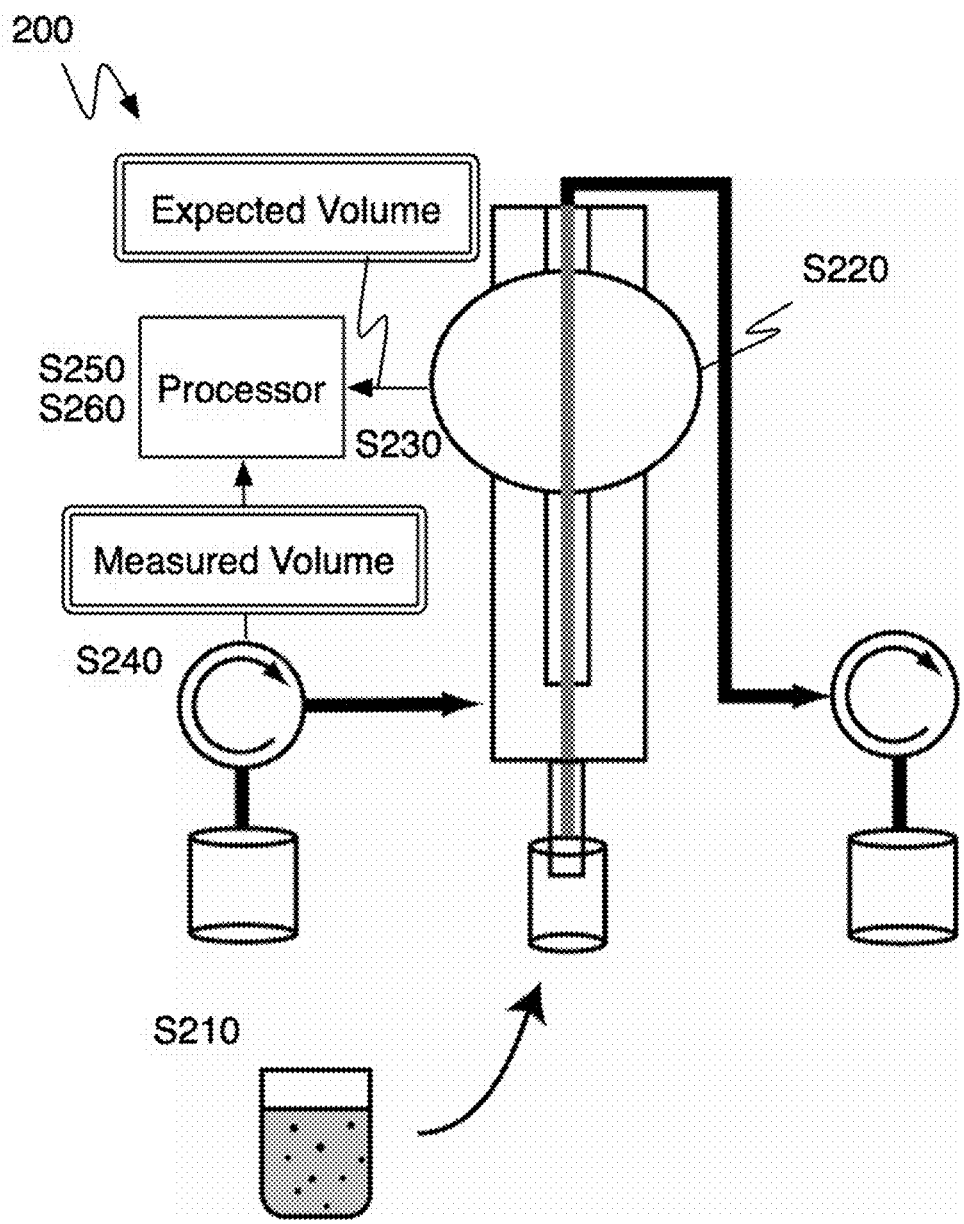
FIG. 2 is schematic representation of a system of the preferred embodiment of the invention.
Figure 3:
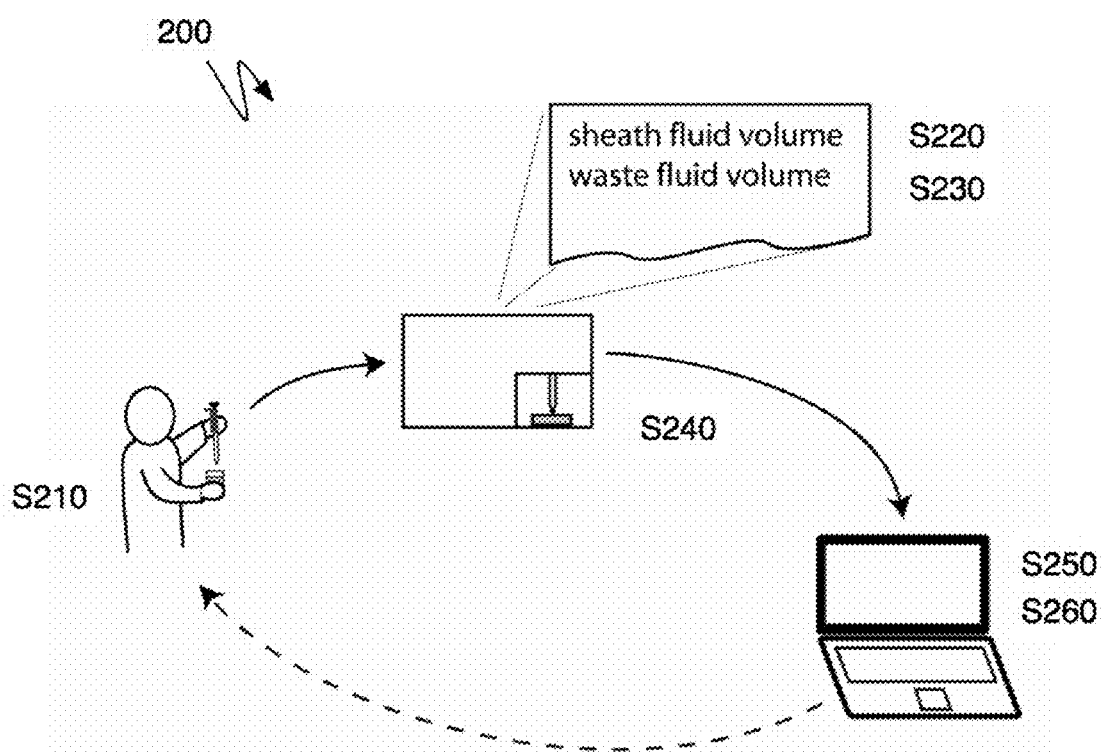
FIG. 3 is a flowchart of a method of a preferred embodiment of the invention.

As shown in FIGS. 2 and 3, a method 200 of verifying the preparation of a sample for a flow cytometer includes preparing a sample fluid with reference beads S210, analyzing a sample fluid S220, determining an expected sample volume from particle analysis S230, measuring a sample fluid volume introduced into a fluidic system S240, comparing the measured sample volume to the expected sample volume S250, and performing an error correction action S260. The method functions to verify the measured sample fluid to meets expected fluid preparation parameters. The method preferably takes advantage of a correlation between the operation of the fluidic system and the volume of sample fluid drawn into the interrogation zone.

Step S210, which includes preparing a sample fluid with reference beads, functions to prepare a sample fluid with an expected reference bead concentration. The sample preferably includes blood, but may be any suitable substance or liquid. The reference beads are preferably included in a reagent(s) of reagents that the experimenter adds to a sample. The reagent(s) with reference beads is preferably prepared in a factory or in a controlled environment and provided to the experimenter. The reagent(s) is preferably designed for a particular test such as the $CD_4$ test. The reference beads may alternatively be added separately by the experimenter or added to the sample fluid in any suitable manner. The reference beads may alternatively be any suitable element that can be used to deduce the expected volume of the sample such as a countable particle with a known concentration in the sample. Additionally, a plurality of distinguishable types of reference beads may be added when preparing the sample fluid. Each type of reference bead is preferably at a known concentration for a particular reagent. A plurality of reagents each with known concentration of reference beads is then preferably mixed or used to prepare a sample fluid. The plurality of reference beads for a plurality of reagents preferably will generate an expected reference bead ratio in the sample fluid.

Step S220, which includes analyzing a sample fluid, functions to perform a flow cytometer analysis of the sample fluid. The sample fluid is preferably hydrodynamically focused through the interrogation zone of the flow cytometer. Particles of interest are preferably analyzed or counted (such as $CD_4$ cells) and the reference beads are additionally counted. Analyzing the sample fluid preferably includes, hydrodynamically focusing the sample fluid and directing a light source at the sample. The light source is preferably a laser light source but any suitable light source may alternatively be used. Multiple detectors arranged around the interrogation zone preferably detect scattered or fluorescent light from the particles. Any suitable optical setup or detection method may alternatively be used to count and analyze the particles of the sample fluid. If a plurality of types of reference beads is included in the sample fluid, each type of reference bead is preferably independently counted. The types of reference beads preferably differ in size or fluorescence such that the flow cytometer can distinguish between the reference beads.

Step S230, which includes determining an expected sample volume from particle analysis functions to calculate the volume of the sample fluid that has been analyzed based on the reference bead count. An expected reference bead concentration of the sample fluid is preferably known (based on the preparation of the sample fluid) such that the expected sample fluid volume can be calculated from the reference bead counted during the flow cytometer analysis. The expected reference bead concentration is preferably collected by a computer system. The expected reference bead concentration may alternatively be calculated from data on the volume of a factory prepared reagents (with reference beads) used, and/or from any suitable preparation data or information. An experimenter or alternatively a sample preparation machine provides the computer system with the reference bead concentration information. In the variation where a plurality of reference beads is prepared in the sample fluid, an expected reference bead ratio is preferably additionally determined. The ratio is preferably dependent on the preparation of the sample fluid. A reference bead ratio is preferably measured by the flow cytometer such that the expected reference bead ratio can preferably be compared to the measured reference bead ratio.

Step S240, which includes measuring a sample fluid volume introduced into a fluidic system, functions to calculate the actual sample fluid that has passed through the interrogation zone. The fluidic system is preferably a peristaltic pump system with a sheath peristaltic pump and a waste peristaltic pump. The fluidic system is more preferably substantially similar to the peristaltic pump system described above. The volume of sheath fluid pumped into the system is preferably calculated from the known flow rate to speed value and the speed of the motor or alternatively, the volume of sheath fluid may be calculated from any suitable characteristics of the peristaltic pump such as motor rotation. The volume of waste fluid is preferably calculated in a substantially similar way. The difference between the volume of waste fluid and the volume of sheath fluid is equal to the volume of sample fluid ($V_{waste} - V_{sheath} = V_{sample}$) introduced through a SIP (as described above). As a variation, the volume pumped by the sheath pump or the waste pump may be a set amount, while the other pump is dynamically changed to control the rate. In this variation, the volume pumped by the dynamically altered pump may be measured. The volume of the sample fluid may alternatively be obtained by monitoring the volume of a sheath fluid container and the volume of a waste fluid container, fluid flow sensors, and/or any suitable volume measuring techniques.

Step S250, which includes comparing the measured sample volume to the expected sample volume, functions to verify the sample fluid is prepared according to the expectations of the experimenter. The expected sample fluid volume ideally will be substantially equal to the actual sample fluid volume for a properly prepared sample fluid. However, the reference bead count will preferably indicate a different volume than was actually passed through the flow cytometer in a case where the sample is improperly prepared. In the variation where a plurality of reference beads is prepared in the sample fluid, the ratio of the types of reference beads is preferably calculated. There may additionally be a threshold for the difference between the expected sample fluid volume and the actual sample fluid volume, which would function to allow for a level of variation in the volumes.

Step S260, which includes performing an error correction action, functions to resolve any errors with the preparation of the sample fluid. The error correction action preferably occurs when the expected sample fluid volume does not match the actual sample fluid volume (i.e., a preparation error). The error correction action preferably includes alerting the experimenter (or any other suitable person) to the occurrence of the preparation error. An allowable preparation error may additionally and/or alternatively be used as a threshold to determine when the experimenter should be notified. The notification preferably occurs on a graphical display, but may alternatively be indicated in the data results, a sound alert, and/or in any suitable manner. The experimenter when informed of the error preferably prepares a new sample, corrects remaining samples, reruns the experiment, and/or performs any suitable action. The error correction action may additionally or alternatively include recommending or performing an experimental change (e.g., adjustment to the preparation of the sample fluid or subsequent sample fluids), accounting for the discrepancy in volumes (e.g., adjusting data results based on actual reagent concentration), and/or performing any suitable course of action based on the volume difference. Alternatively, an action may be performed when the expected sample fluid volume prediction is sufficiently equal to the measured sample fluid volume. Any suitable action may be performed based on the equality or inequality of the expected sample fluid volume and the measured sample fluid volume.

3. System and Method of the Alternative Embodiments

Figure 4:
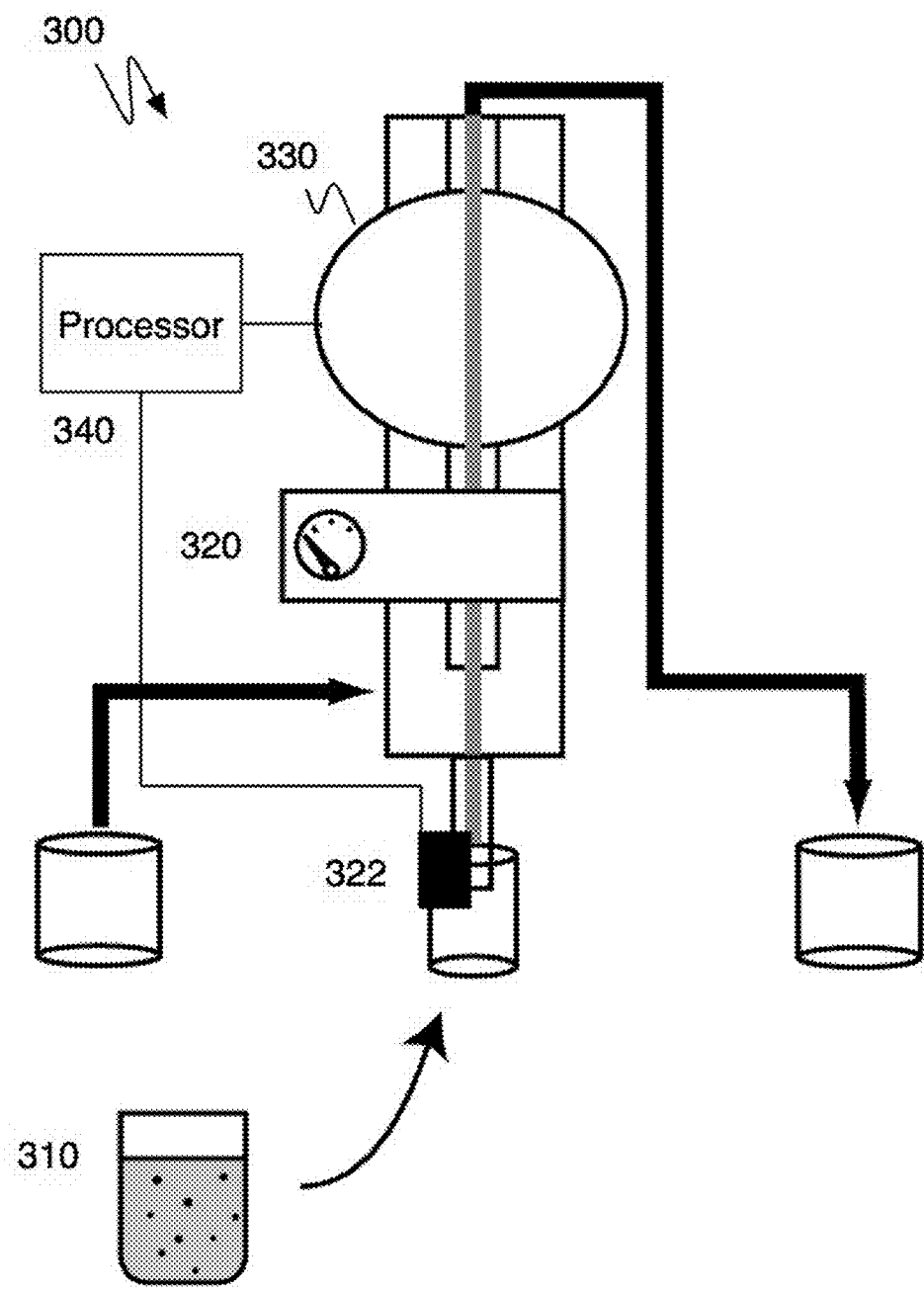
FIG. 4 is a schematic representation of a system of the preferred embodiment of the invention.

As shown in FIG. 4, the flow cytometer system 300 of the alternative embodiments for the verification of a prepared sample includes a sample fluid prepared with beads 310, a volume sensing fluidic system 320, an interrogation zone 330, and a processor 340. The flow cytometer system 300 functions to compare the actual sample volume as determined by the volume sensing fluidic system to the expected volume of the prepared sample (as indicated by the reference beads in the sample). Discrepancies in these two volume measurements are preferably handled by flagging data, alerting the experimenter, correcting for volume discrepancies, modification of a sample, and/or any suitable response. Except for the substitution of the volume sensing fluidic system for the peristaltic pump system, the flow cytometer system of the alternative embodiment is substantially similar to the flow cytometer system of the preferred embodiment.

Figure 6A:
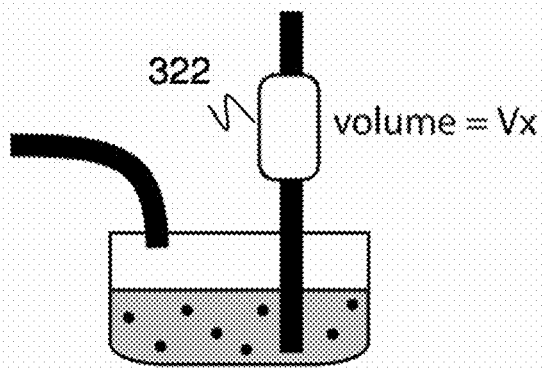
FIGS. 6A-6C are schematic representations of variations of direct volume sensing fluidic systems.
Figure 6B:
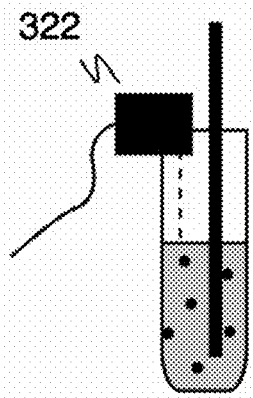
Figure 6C:
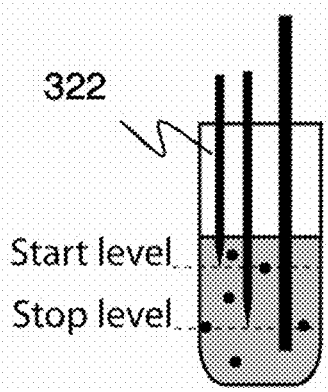
Figure 7A:
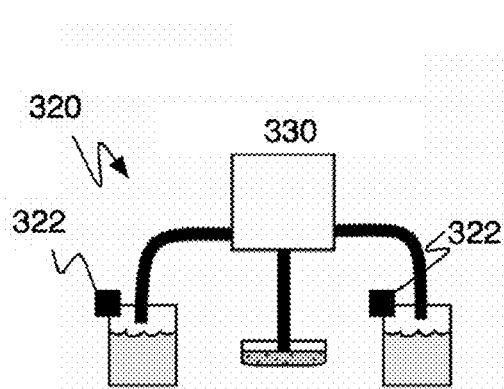
FIGS. 7A-7C are schematic representations of variations of indirect volume sensing fluidic systems.
Figure 7B:
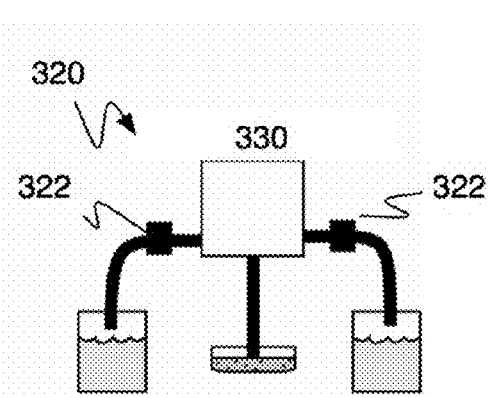
Figure 7C:
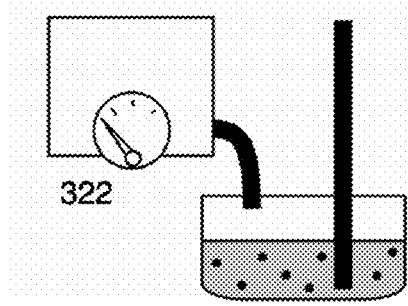

The volume sensing fluidic system 320 of the alternative embodiments functions to measure the volume of sample fluid analyzed by the flow cytometer. The fluidic system of a flow cytometer preferably functions to hydrodynamically focus a sample fluid into an interrogation zone. A sheath fluid is preferably used to hydrodynamically focus the sample fluid, and a sheath and sample fluid mixture is preferably deposited as a waste fluid into a waste container. However, any suitable fluidic system may alternatively be used. The volume sensing fluidic system preferably uses the operation data of components of a flow cytometer such as motor speed, motor rotation, pump pressure, fluidic pressure, sample cycles, and/or any suitable fluidic system operational data. Alternatively, the volume sensing fluidic system may include additional sensors to a fluidic system, an add-on device for a fluidic system, and/or be any suitable device. As shown in FIGS. 6A-6C, the volume sensing fluid system of a first variation measures the sample fluid volume with a direct system (i.e., a system that measures the sample fluid). As shown in FIGS. 7A-7C, the volume sensing fluid system of a second variation, however, measure the sample fluid volume with an indirect system (i.e., a system that measures other fluid volumes to deduce the actual sample fluid volume). The indirect system may be similar to the variations described above except applied to sheath fluid and/or waste fluid. The volume sensing fluid system may alternatively measure the sample fluid volume in any suitable manner.

As shown in FIGS. 6A-6C, the direct system preferably functions to actively measure the sample fluid volume. In one version, a direct system is used in a fluidic system that incorporates an air and/or vacuum pump to pressurize and pump sheath fluid from a high-pressure container to the interrogation zone of a flow cell. A syringe, container, or reservoir is preferably filled with the sample before introduction to the interrogation zone. The syringe functions to allow for dispensing precise volumes of fluid. The syringe preferably has a known volume, and the syringe is preferably filled to this known volume for each introduction of the fluid into the fluidic system. The volume of the actual sample fluid volume analyzed is thus a multiple of the syringe volume, and is dependent on the number of times a full syringe volume was introduced into the system. In another version, a sample fluid container with well-defined volume levels (e.g., a test tube with a large height to diameter ratio) is used in cooperation with a container volume sensor 322. Two or more fluid level sensors may alternatively be used to sense the volume of a sample between one or more levels as shown in FIG. 6C. The sample fluid is preferably run through the flow cytometer until the sample fluid container reaches a start level of fluid at a first level sensor (the start level sensor). The sample fluid is then run through the system with the flow cytometer preferably performing the analysis. A second level sensor (the stop level sensor) is preferably located at a lower level than the start level sensor. The stop level sensor preferably indicates when the sample fluid in the container has reached the stop level. The volume of sample fluid between the start and stop level sensor is preferably known value. The sample container may alternatively have a calibrated volume profile. A volume profile preferably includes any suitable data such that the level or level change of a fluid within the sample container can be used to calculate the volume of fluid remaining in the sample container or removed from the sample container. The container volume sensor 322 functions to measure the volume of sample withdrawn from the fluid container as shown in FIG. 6B. The container volume sensor 322 may be a distance sensor perpendicularly inspecting the surface of the sample fluid in the sample container, a resistive or capacitive sensor inspecting the fluid level in the sample container, an image system inspecting the surface and/or side profile of the sample container, and/or any suitable sensor to measure the volume of the sample fluid in the fluid container. The direct system may alternatively include any device that directly measures the sample fluid withdrawn from a container or passing through the fluidic system. The direct system may include an intake sensor along the main channel through which the sample fluid is introduced to the fluidic system, as shown in FIG. 6A. The intake sensor is preferably coupled to the SIP or drawtube before the interrogation zone 330. The intake sensor preferably measures the volume, flow rate, or any suitable parameter to deduce the volume of sample fluid introduced to the system.

As shown in FIGS. 7A-7C, the indirect system preferably calculates a sample fluid volume by calculating the volume of other fluids through the fluidic system. Preferably the sheath fluid volume and/or the waste fluid volume are measured. The waste fluid is preferably the sum of a sample fluid and sheath fluid. The sample volume is preferably calculated by subtracting the measured sheath fluid volume and the waste fluid volume. The volume of a collection fluid (fluid separated from the waste fluid) may additionally be measured, and the sheath fluid is subtracted from the sum of the waste fluid and collection fluid. Any number of volumes may alternatively be measured and the sample fluid volume may be calculated by subtracting appropriate volumes from a sum total volume. In one version, the volumes of a sheath container and a waste container may include sensors to measure the volume introduced and removed from the system. A fluid with a known fluidic flow relationship with the sample fluid may alternatively be used. In another version, the sample fluid volume may be calculated using a sheath to sample fluid ratio based on pumping pressure. The indirect system may alternatively use the variations described above, but applied to the sheath fluid, waste fluid, collection fluid, and/or any suitable fluids.

Figure 5:
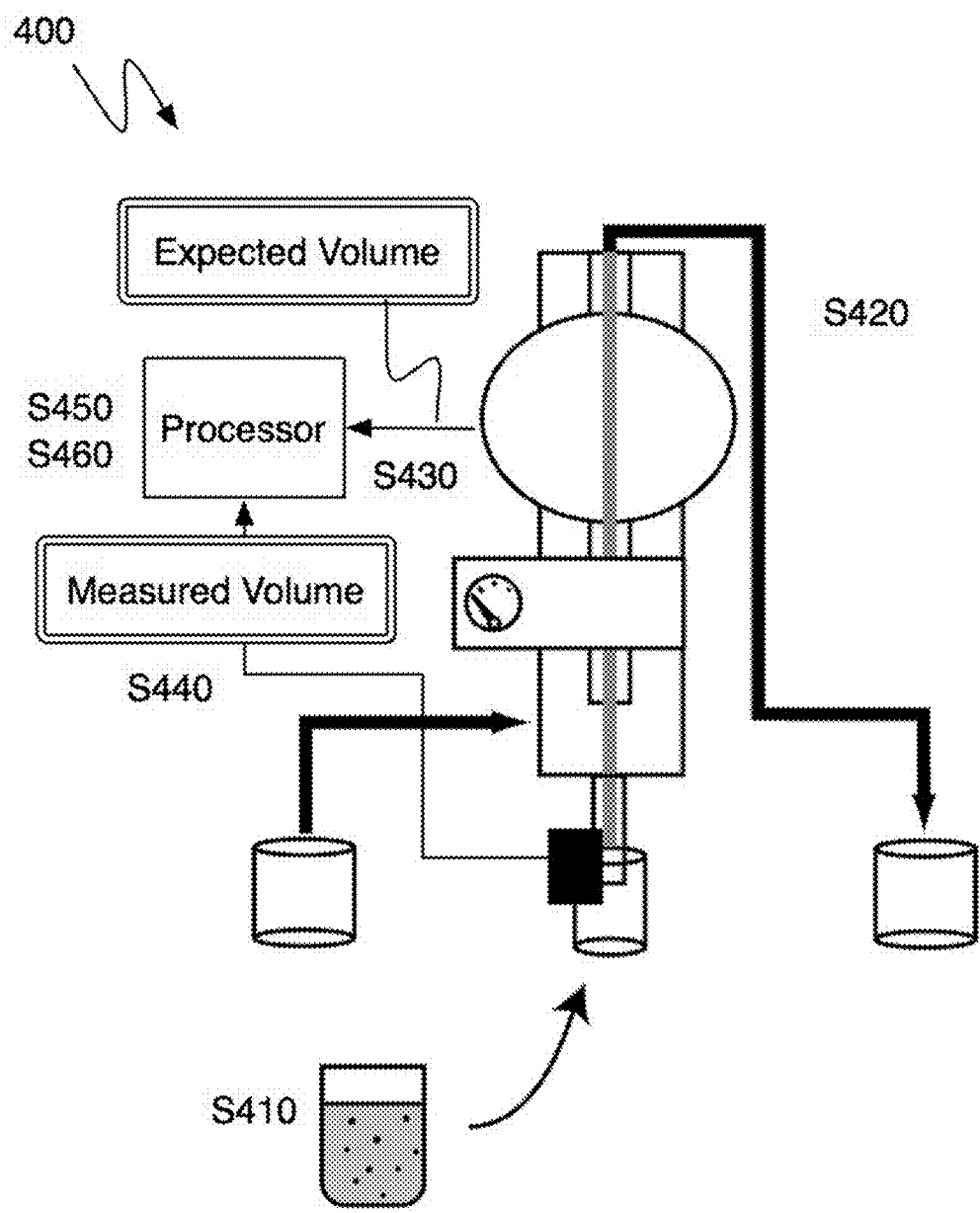
FIG. 5 is schematic representation of a system of the preferred embodiment of the invention.

As shown in FIG. 5, the method 400 of verifying the preparation of a sample for a flow cytometer of the alternative embodiments includes preparing a sample fluid with reference beads S410, analyzing a sample fluid S420, determining an expected sample volume from particle analysis S430, measuring a sample fluid volume introduced into a fluidic system S440, comparing the measured sample volume to the expected sample volume S450, and performing an error correction action S460. The method functions to verify the measured sample fluid to the desired preparation. Except for the substitution of a new Step S440, the method of the alternative embodiment is substantially similar to the method 200 of the preferred embodiment.

Step S440 of the alternative embodiments, which includes measuring a sample fluid volume introduced into a fluidic system, functions to calculate the actual sample fluid that has passed through the interrogation zone. The fluidic system is preferably any fluidic system commonly used in a flow cytometer such as a flow cytometer that incorporates an air and/or vacuum pump to pressurize and pump sheath fluid from a high-pressure container to the interrogation zone of a flow cell. The fluidic system of a flow cytometer preferably functions to hydrodynamically focus a sample fluid in an interrogation zone. A sheath fluid is preferably used, and the sheath and sample fluid mixture is preferably deposited as a waste fluid. However, any suitable fluidic system may alternatively be used. The volume sensing fluidic system preferably uses the operation data of components of a flow cytometer such as motor speed, motor rotation, pump pressure, fluidic pressure, sample cycles, electrical sensor data, and/or any suitable fluidic system operational data. Alternatively, the volume sensing fluidic system may include additional sensors to a fluidic system, an add-on device for a fluidic system, and/or be any suitable device. The volume sensing fluid system preferably measures the sample fluid volume with a direct system. The direct system preferably measures the sample fluid directly. The direct system is preferably substantially similar to the one described above. In one variation of a direct system, discrete and precise volumes of the sample fluid may be introduced to the system, and the actual sample volume will always be a known multiple of the precise volume. In another variation of a direct system, a sensor may measure the volume of sample fluid withdrawn from a container (such as a beaker). Any suitable variation of a direct system may be used such as sensing fluid flow, fluid velocity, and/or any suitable method of sensing the sample fluid volume introduced into the fluidic system. The volume sensing fluid system may alternatively measure the sample fluid volume with an indirect system. The indirect system preferably measures or calculates multiple fluid volumes to deduce the sample fluid volume. More preferably, the indirect method subtracts the sheath fluid from the waste fluid. Though any suitable fluids introduced into the system may be used including other liquids and/or gases. In one variation, electric sensors are used to monitor the volumes of a sheath container (where sheath fluid is stored before being introduced into the system) and the volumes of a waste container (where waste fluid is deposited after analysis). The sheath fluid volume (fluid introduced into the system) is then subtracted from the waste fluid to calculate the actual sample fluid volume. In another variation a fluid process is monitored that can be used to calculate the actual sample fluid volume. The other fluid process (such as pump pressure) preferably relates to the precise amount of sample fluid introduced into the flow cytometer.

As a person skilled in the art will recognize from the previous detailed description and from the figures and claims, modifications and changes can be made to the preferred and alternative embodiments of the invention without departing from the scope of this invention defined in the following claims.

We claim:

1. A method for verifying preparation of a sample fluid drawn into an interrogation zone of a flow cytometer, comprising:
    receiving the sample fluid prepared with a reference bead concentration;
    drawing a sample volume of the sample fluid with the reference bead concentration into the interrogation zone with a peristaltic pump system;
    analyzing the sample volume of the sample fluid in the interrogation zone to determine a parameter indicative of reference bead count;
    determining an expected value of the sample volume based upon the parameter and the reference bead concentration;
    determining a measured value of the sample volume of the sample fluid used to determine the expected value; and
    performing an error correction action in response to a comparison between the measured value of the sample volume and the expected value of the sample volume.

2. The method of claim 1, wherein drawing a sample volume of the sample fluid into the interrogation zone with a peristaltic pump system further comprises drawing the sample volume using a sheath pump and a waste pump, wherein a pressure differential created by the sheath pump and the waste pump draws the sample fluid into the interrogation zone.

3. The method of claim 2, wherein determining a measured value of the sample volume comprises determining a measured value based on a difference between a sheath fluid volume pumped by the sheath pump and a waste fluid volume pumped by the waste pump.

4. The method of claim 3, wherein drawing a sample volume of the sample fluid into the interrogation zone includes simultaneously:
    pumping the sheath fluid volume, with the sheath pump, from a sheath container into the interrogation zone and
    pumping the waste fluid volume, with the waste pump, from the interrogation zone into a waste container;
        wherein the interrogation zone is in fluid communication with the sheath pump, the waste pump, and a sample container containing the sample fluid, and
        the sheath pump is configured to pump at a first flow rate and the waste pump is configured to pump at a second flow rate thereby creating the pressure differential to draw the sample fluid from the sample container into the interrogation zone.

5. The method of claim 3, wherein analyzing the sample volume of the sample fluid to determine a parameter indicative of reference bead count includes directly counting reference beads based upon optical detection.

6. The method of claim 1, wherein receiving the sample fluid prepared with a reference bead concentration includes receiving a blood sample with a CD4 test reagent including reference beads, and wherein analyzing the sample volume of the sample fluid includes enumerating reference beads of the reagent and CD4 cells.

7. The method of claim 1, wherein analyzing the sample volume of the sample fluid in the interrogation zone to determine a parameter indicative of reference bead count comprises directly counting reference beads based upon optical detection.

8. The method of claim 1, wherein analyzing the sample volume of the sample fluid in the interrogation zone to determine a parameter indicative of reference bead count further comprises determining a time based function of a reference bead count.

9. The method of claim 1, wherein receiving the sample fluid prepared with a reference bead concentration comprises receiving a sample fluid prepared with a first reference bead concentration and a second reference bead concentration.

10. The method of claim 9, wherein analyzing the sample volume of the sample fluid in the interrogation zone to determine a parameter indicative of reference bead count further comprises determining a ratio between a first reference bead parameter and a second reference bead parameter.

11. The method of claim 1, wherein determining a measured value of the sample volume of the sample fluid comprises calculating a difference between a waste fluid volume and a sheath fluid volume.

12. The method of claim 1, wherein determining a measured value of the sample volume of the sample fluid comprises directly measuring a volume of sample fluid drawn using a sensor.

13. The method of claim 1, wherein performing an error correction action comprises providing a user notification in response to a comparison between the measured value and the expected value of the sample volume.

14. The method of claim 13, wherein providing a user notification comprises providing an alert indicating sample preparation error.

15. A method for verifying preparation of a sample fluid drawn into an interrogation zone of a flow cytometer, comprising:
    drawing a sample volume of the sample fluid, prepared with a reference bead concentration, into the interrogation zone with a peristaltic pump system;
    analyzing the sample volume of the sample fluid in the interrogation zone to determine a parameter indicative of reference bead count;
    determining an expected vale of the sample volume based on the parameter and the reference bead concentration;
    determining a measured value of the sample volume of the sample fluid used to determine the expected value; and
    providing a user notification in response to a comparison between the measured value and the expected value of the sample volume.

16. The method of claim 1, wherein performing an error correction action comprises at least one of providing a user notification and performing an adjustment to a preparation of the sample fluid in response to the comparison between the measured value and the expected value of the sample volume.

* * * * *